United States Patent [19]

Straus et al.

[11] 3,951,823
[45] Apr. 20, 1976

[54] FOAM WELL CLEANOUT USING OLIGOMERIC SULFONATES

[75] Inventors: Alan E. Straus, El Cerrito; William A. Sweeney, Larkspur; Ralph House, El Sobrante; Samuel H. Sharman, Kensington, all of Calif.

[73] Assignee: Chevron Research Company, San Francisco, Calif.

[22] Filed: Sept. 25, 1974

[21] Appl. No.: 509,176

Related U.S. Application Data

[60] Continuation of Ser. No. 276,266, July 28, 1972, abandoned, which is a division of Ser. No. 858,097, Sept. 15, 1969, Pat. No. 3,721,707.

[52] U.S. Cl. .............................. 252/8.5 C; 166/309; 175/69; 252/8.55 B; 252/307; 252/530; 252/535; 252/549; 252/554; 260/513 R
[51] Int. Cl.² ..................... C09K 7/02; E21B 43/22
[58] Field of Search ............ 252/8.5 C, 8.55 B, 307; 175/65, 69, 71

[56] References Cited

UNITED STATES PATENTS

| | | |
|---|---|---|
| 3,444,087 | 5/1969 | Eccles et al. ........................ 260/513 |
| 3,463,231 | 8/1969 | Hutchison et al. ................... 166/303 |
| 3,486,560 | 12/1969 | Hutchison et al. ................ 252/8.5 X |
| 3,572,439 | 3/1971 | Hutchison et al. ................ 252/8.5 X |
| 3,721,707 | 3/1973 | Straus et al. ........................ 260/513 |

*Primary Examiner*—Herbert B. Guynn
*Attorney, Agent, or Firm*—G. F. Magdeburger; John Stoner, Jr.

[57] ABSTRACT

Organic disulfonic acids are produced by heating a sulfonate monomer at a temperature above 110°C. in the substantial absence of water. Olefin sulfonation product mixtures, hydroxyalkane sulfonic acids, alkane sultones, alkene sulfonic acids and mixtures thereof are oligomerized under these conditions.

6 Claims, No Drawings

FOAM WELL CLEANOUT USING OLIGOMERIC SULFONATES

CROSS-REFERENCE TO RELATED APPLICATIONS

This application is a continuation of application Ser. No. 276,266, filed July 28, 1972, now abandoned, which, in turn, is a division of application Ser. No. 858,097, filed Sept. 15, 1969, now U.S. Pat. No. 3,721,707 issued Mar. 20, 1973.

BACKGROUND OF THE INVENTION

1. Field of the Invention

This invention relates to a process for the production of organic sulfonic acid oligomers and to the novel compositions produced in the process, particularly sulfonic acid oligomers from straight chain precursor compounds.

2. Description of the Prior Art

It is known to prepare organic sulfonic acids by the reaction of sulfur trioxide with mono-olefinic hydrocarbons in the liquid phase at a temperature below about 100°C., usually below about 50°C., by either contacting the olefin with attenuated sulfur trioxide, that is with gaseous sulfur trioxide which has been diluted with a relatively inert gas, usually air, or with sulfur trioxide which is modified by complexing with an organic ether, acid, acid anhydride, a phosphate ester, or the like. In general, the resulting sulfonate reaction product mixture only contains a minor amount of organic sulfonic acid, usually alkene sulfonic acid, and a major amount of alkane sultones. Additional sulfonic acid can be obtained by hydrolysis of the sulfonation reaction mixture by treatment with aqueous caustic or aqueous mineral acid. When aqueous caustic is employed, the resulting product is a complex mixture which is mainly alkene sulfonate and hydroxyalkane sulfonate. Where acid is employed, the product is a mixture of alkene sulfonic acid and hydroxyalkane sulfonic acid. In the case of the caustic hydrolysate the corresponding sulfonic acid can be obtained by acidification with strong mineral acid and extraction with a suitable organic solvent. The hydroxy sulfonic acids, however, readily revert under acid conditions to sultones with mild heating.

The neutralized sulfonic acids obtained by the use of alpha olefins are excellent surface active agents, and are particularly useful for the production of foamed well circulation fluids. However, aqueous concentrates of these materials tend to solidify and separate into solid and liquid phase mixtures under the temperature conditions encountered in the field.

A more direct process for the production of organic sulfonic acids is desirable for reasons of cost.

A process for the production of organic sulfonic acids substantially free of hydroxy substituents is desirable in order to avoid sultone formation.

An aqueous organic sulfonate detergent concentrate which does not separate into a mixture of solid and/or liquid phases or does so only at very low temperatures is desirable for use in the foamed well circulation fluid art. [See, for example, copending U.S. application Ser. No. 704,832, filed Feb. 12, 1968, now U.S. Pat. No. 3,463,231, issued Aug. 26, 1969.]

SUMMARY OF THE INVENTION

It has now been found that an organic sulfonic acid oligomer mixture can be prepared by heating in the liquid phase a feed containing one or more compounds having a carbon atom content in the range from about 5 to 1000 carbon atoms of the types and formulas:

a. sultones, $R^2(-O\overset{|}{S}O_2)$ 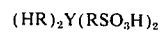
b. hydroxysulfonic acids, $R^2(-SO_3H)(-OH)$
c. unsaturated sulfonic acids, $R[R^2(-CH=CH-)]-SO_3H$ in which R is hydrogen or a monovalent hydrocarbon radical, and $R^2$ is a divalent hydrocarbon radical, and in which the R and $R^2$ groups contain no nonaromatic carbon-carbon double- or triple-bond unsaturation. The heating is continued for a period of time sufficient for at least a significant conversion of the feed, a period which is usually in the range from about 1 minute to 25 hours.

Surprisingly, when the feed is heated above about 110°C. in the substantial absence of water, i.e., where the water content of the heated mixture is less than about 5–10 per cent by weight, the oligomerization reaction, a dimerization and/or intercondensation, occurs which results in the production of a mixture of molecular species having an average molecular weight wich is approximately double that of the original feed. The resulting oligomer product appears to be mainly a mixture of novel disulfonic acids of the formula $(HR)_2Y(RSO_3H)_2$ in which the several R groups are the same or different alkanediyl radicals and Y is a radical of the group 1,1,2,2-ethanetetrayl, 1,2,4,5-benzenetetrayl, or 1,2,4,5-cyclohexanetetrayl. The total number of carbon atoms contained by these disulfonic acid oligomers is equal to the sum of the carbon atom contents of the two precursor monomers participating in the oligomerization reaction. Structural representations of the foregoing oligomers include the following:

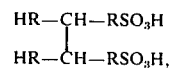

and

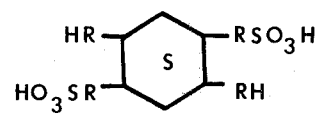

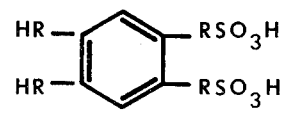

i.e., including head-to-head and head-to-tail oligomerization of the monomers.

In view of the difunctionality of the subject oligomers, they are particularly useful for the production of linear polymers, particularly those obtainable from disulfonyl halide derivatives of the subject oligomers, for example:

1. $R(SO_2Cl)_2 + H_2N(CH_2)_6NH_2$ polysulfonamide polymer.

Other polyfunctional comonomers, such as organic diols, polyols, etc., may also be employed for the preparation of useful polymers and resins from the oligomeric polysulfonates of the instant invention.

DESCRIPTION OF THE INVENTION

In a preferred embodiment of the present invention a mixture of oligomerizable compounds is used, namely the crude reaction product mixture resulting from sulfonating an n-alkene, for example 1-hexadecene, with vaporized sulfur trioxide which has been diluted with air. When the conversion of the olefin to sulfonate is substantially complete (requiress about 1.20 mols of $SO_3$ per mol of olefin), the product mixture is heated to 155°–160°C. and maintained at this temperature for 1–1.5 hours. Infrared and/or nuclear magnetic resonance (NMR) spectra analyses demonstrate that the resulting mixture contains little or no hexadecene sulfonic acid, hydroxyhexadecane sulfonic acid or hexadecane sultone, the foregoing being the principal components of the sulfonated hexadecene feed.

Molecular weight and other characterizing determinations demonstrate:

1. that the product has a molecular weight corresponding to a $C_{32}$-disulfonic acid;
2. the product is a molecular mixture of which about 15 mol per cent contains a benzene ring, another substantial fraction contains a cyclohexane ring, and a third substantial fraction is a carbon-carbon bond-bridged hexadecyl dimer containing no unsaturation; and
3. the oligomeric disulfonic acid mixture per se is a useful foaming agent as are likewise the water soluble salts of the acid.

In view of the nature of the product composition, it is clear that a number of chemical reactions are occurring in the present process (including dimerization by reaction between two like monomers), intercondensation (reaction between dissimilar monomers, i.e., homologs), acyclic cyclization, aromatization and intra molecular transfer of hydrogen.

The temperature required to effect the oligomerization of the process is in the range above about 110°C. As the temperature is increased, the reaction rate becomes faster. Preferred temperatures are in the range 120°C.–200°C. Higher temperatures may be employed advantageously provided that carbonization and degradation of the feed does not become a problem, a matter which varied depending upon the particular feed and usually occurs appreciably in the range 250°C.–300°C.

The course and degree of completion of the present oligomerization reaction is conveniently followed by spectral analysis methods, particularly nuclear resonance (NMR) spectra of particular hydrogen atoms of the feed and product mixture. In the course of the reaction the following functional groups are eliminated from the product: (1) the sultone groups, (2) the carbon-carbon olefinic double bond unsaturation, and (3) the alkanol hydroxy groups; thus the adsorption arising from: (1) protons alpha to the sultone C—O bond (usually in the range 4.4–4.6 ppm), (2) vinyl protons (usually in the range 5.0–5.9 ppm), and (3) protons alpha to the C—O bond of alkanol groups (usually in the range 3.4–3.7 ppm) decrease as the reaction proceeds and approach or become zero when conversion is complete. Similarly, characteristic adsorptions of the aforementioned functional groups of the feed and product mixtures in the infrared spectrum may also be conveniently employed to follow the conversion. Thus, the 1,3-sultones absorb significantly at 1330–1350, 1190, 1155, 1000, 940, 815–880 and 620 cm$^{-1}$. The 1–4 sultones absorb significantly at 1330–1360, 1160, 895, 810–825 and 530 cm$^{-1}$. Vinyl unsaturated sulfonic acids adsorb significantly at 1700, 1165, 1040, 965 and 910 cm$^{-1}$. The degree of conversion of the feed is conveniently approximated by comparing the before and after spectra of the feed and product using one or more of the above-noted characteristic adsorbances. For example, the ratio of the areas under the NMR spectral curves as follows:

$$\frac{[2(3.4-3.7 \text{ ppm} + 4.4-4.6 \text{ ppm}) + 5.0-5.9 \text{ ppm}]_{product\ mixture}}{[2(3.4-3.7 \text{ ppm} + 4.4-4.6 \text{ ppm}) + 5.0-5.9 \text{ ppm}]_{feed}}$$

is a measure of the unconverted feed. Conversely, as used herein, when the foregoing ratio has decreased to less than 0.90 to 1, then by definition a significant conversion of feed to oligomer product has occurred. Similar comparisons may be used employing the other characteristics adsorbances noted above.

In addition to the foregoing characteristic spectral adsorbances, as noted above, disulfonic acids containing benzene rings and cyclohexane rings are produced in the subject reaction. This results in new or additional characteristic spectral adsorbances arising, for example, from hydrogen attached to a carbon atom which is a part of a benzene nucleus. These adsorbances, particularly in the NMR spectra, may also be employed to mark the degree of completion of the process.

By oligomerization, as used herein, is meant dimerization of like monomers and intercondensation of unlike monomers.

By longest straight chain of the compound, as used herein, is meant the determination as in conventional practice which is employed in the naming of organic compounds.

The length of time required for conversion of the feed to oligomer varies depending upon the monomer or monomeric mixture employed and the temperature of the heating. For example, using an n-$C_{15-18}$ alpha olefin sulfonation product feed, the following representative time-temperature relationship was noted:

| Temp, °C. | Time, Hrs. | Completion, % of Theory |
|---|---|---|
| 100 | 28 | 0 |
| 120 | 28 | 91 |
| 140 | 4 | 87 |
| 160 | 1 | 85 |
| 170 | 0.3 | est.~85 |

Thus, in view of the foregoing, the time required for substantially complete conversion (90 percent plus), in general, will be in the range from about 0.1 to 30-50 hours and for the preferred temperature range, 140°C. to 170°-200°C., in the range from about 0.1 to 5 hours. Where partial conversions are desired, relatively shorter reaction periods are employed.

An induction period for the oligomerization which varies dependng upon the particular feed is especially notable at reaction temperatures in the range below about 130°-155°C. Thus at 120°C. this period may be as much as 1-2 hours. As this temperature is raised, the induction period becomes shorter and above about 160°C. is scarcely, if at all, appreciable. The use of the aforedescribed spectral analysis technique as a means of following the course of the reaction disposes of any ambiguity which might arise in view of the induction phenomenon.

Usually the process of the invention is effected more advantageously in the absence of inert diluents, for example saturated hydrocarbons or mixtures thereof, but these may be employed to advantage, for example where heat exchange or temerature control is a problem.

Strong mineral acid appears to promote the instant oligomerization reaction, particularly in the case of the sultone feed compounds. In the case of the preferred sulfur trioxide-olefin reaction mixture feeds, from 1-5 weight per cent of sulfuric acid is ordinarily present and the presence of additional mineral acid does not appear to improve the rate of the reaction. However, the crude oligomerization reaction product mixtures ordinarily are quite dark colored and the presence of phosphoric acid in the heated mixture usually reduces the color. Sulfuric acid is preferred.

A wide variety of bifunctional organic compounds are suitable alone or in admixture as feeds for the present oligomerization reaction. They must contain at least about 5 nonaromatic carbon atoms per molecule, a sulfonate functional group, i.e., $-SO_3-$, and one of the following: (1) a carbon-carbon double-bond, i.e., $-CH=CH-$; (2) an alkanol hydroxy group, or a sulfonate ester group of which the above sulfonate group is a component, i.e., a sultone, and the functional groups must be substituents attached to non-aromatic carbon atoms with the balance being carbon and/or hydrogen. For practical purposes, the feed compounds will usually contain less than about 1000 carbon atoms per molecule, and preferably less than about 50. More preferably the feed compounds have straight chain carbon skeletons and a carbon atom content in the range 5 to 30.

Representative classes of compounds suitable for use as feeds for the subject process include sultones, $R^2(O-SO_2)$; hydroxy sulfonic acids, $R^2(-OH)(-SO_3H)$; and unsaturated sulfonic acids, $R[R^2(-CH=CH-)]-(-SO_3H)$ in which R is hydrogen or a monovalent hydrocarbon radical and $R^2$ is a divalent hydrocarbon radical, the feed compound(s) having a carbon atom content in the range from about 5 to 1000 and containing no non-aromatic carbon-carbon double or carbon-carbon triple bond unsaturation, and mixtures thereof. Preferred representative classes of feeds for the process herein are of the formulas a) 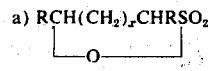

b. $RCH(OH)(CH_2)_x CHRSO_3H$, and c. 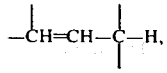

in which $x$ is in the range 0-3, inclusive, and $y$ is in the range $0-n$, with $n$ being a number which is 4 less than the number of carbon atoms in the longest straight chain of the compound which contains the $-SO_3H$ group as a substituent, and in which the groups may be the same or different and are hydrogen or an alkyl group. Mixtures of these classes and/or homologs are suitable feeds.

Preferred process feeds for use herein, for reasons of cost and availability, are the crude reaction product mixtures obtained by the sulfonation of a mono-olefinic hydrocabon feed using sulfur trioxide as known in the art [cf U.S. Pat. Nos. 2,061,617; 2,094,451; 2,572,605; 3,444,191, etc., as well as Ind. and Eng. Prod. Research & Development, Volume 2, No. 3, Pp. 229-231 (1963)]. Briefly, in sulfur trioxide sulfonations the liquid olefin, either neat or dissolved in an inert medium, is contacted with from about 0.5 to 1.5, usually from about 0.8 to 1.3, mols of sulfur trioxide. The sulfur trioxide is added in a variety of ways:

1. vaporized and diluted with an inert gas, usually air;
2. complexed with an organic compound, for example dioxane, acetic acid or anhydride, etc.; or
3. as a solute in an inert medium for example, liquid sulfur dioxide, hexane, etc.

Since the olefin sulfonation reaction is exothermic, the reaction mixture temperature is generally maintained below about 65°C., usually below 50°C., by a cooling means. Somewhat higher local temperatures (as high as 150°C.) usually prevail briefly at the zone of initial contacting of the reactants where air-sulfur trioxide sulfonation mixtures are employed. In these reactions, mono-olefinic hydrocarbons containing at least one allylic hyrogen, i.e.,

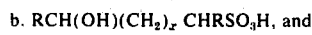

are in general sulfonatable by the use of sulfur trioxide and although actual crude or processed product mixtures vary depending upon the particular combination of process variable employed, the product is in general a satisfactory feed for the instant oligomerization process provided that the water content of the feed is less than 5-10 weight per cent. Excess water, if present, can be readily removed by conventional drying means.

Representative feeds satisfactory for use in the present oligomerization process include the sulfur trioxide-olefin sulfonates derived from sulfonatable mono-olefinic hydrocarbons such as hexadecene-1, heptadecene-2, octadecene-3, hexene-1, ethylene-growth olefins, cracked wax alpha-olefins of the $C_5-C_{20}$ molecular range and fractions thereof; olefins obtained by dehydrohalogenation of hydrocarbon halides; internal olefins obtained by partial or complete double-bond isomerization, i.e., partial or complete equilibration; pentacontene, tetracontene, triacontene, eicosene; substituted olefins such as 9-methyldecene-1, 8-cyclohexylundecenc-2, 10-phenyldecene-3, 7,8,9,10-tetramethylundecene-1, 19-methyleicosene, 19-ethyleicosene-5, 4-isopropylpentadecene-1, 7-methyloctene-1; dimers and trimers (oligomers) of lower substantially straight chain olefins such as 2-butyloctene-1, 2-hexyldecene-1; and the like mono-olefinic hydrocarbons.

Representative unsaturated hydrocarbon sulfonic acids suitable for use herein include hexadecene sulfonic (all isomers singly or in admixture), n-$C_6$-$C_{20}$-alkene sulfonic (molecular mixtures, fractions thereof and/or isomeric mixtures), n-hexene sulfonic, 11-methyl-1-sulfonic-dodecene-3, 6-cyclohexyl-1-sulfonic-hexene-2, 6-phenyl-1-sulfonic-heptene-4, eicosene sulfonic, pentacontene sulfonic, and the like acids.

Representative hydroxyalkane sulfonic acids suitable for use herein include 4-hydroxyoctadecane-1-sulfonic acid, 5-hydroxyoctane-3-sulfonic acid, 19-methyl-4-hydroxyeicosane-1-sulfonic acid, 7,8,9,10-tetrmethyl-5-hydroxyundecane-2-sulfonic acid, 6-cyclohexyl-4-hydroxy-heptane-1-sulfonic acid, 9-hydroxydecane-1 sulfonic acid, 4-isopropyl-3-hydroxypentadecane-1-sulfonic acid, 16-phenyl-3-hydroxyheptadecane-2-sulfonic acid, 5-hydroxypentacontane-1-sulfonic acid, 4-hydroxy-tetracontane-2-sulfonic acid, 3-hydroxytriacontane-1-sulfonic acid; 18-hydroxyeicosane-2-sulfonic acid, 4-hydroxycyclohexane-1-sulfonic acid, and the like hydroxy-sulfonic acids.

Representative suitable feeds for use herein include sultones of the corresponding hydroxysulfonic acids, i.e., beta-, gamma-, delta- and epsilon-sultones of 2-, 3-, 4-, and 5-hydroxyalkane sulfonic acids such as 2-hydroxyoctadecane-1-sulfonic, 6-hydroxyeicosane-2-sulfonic, 6-hydroxy-11-phenyl-heptadecane-3-sulfonic, 5-hydroxyhexane-1-sulfonic, 3-hydroxynonadecane-1-sulfonic, 4-hydroxy-11-methyltetradecane-8-sulfonic, 3-hydroxyoctadecane-1-sulfonic, 4-hydroxypentadecane-2-sulfonic, 4-hydroxytridecane-1-sulfonic, 3-hydroxynonane-1-sulfonic, 9-cyclohexyl-4-hydroxydecane-1-sulfonic, 4-hydroxypentacontane-1-sulfonic, 10-phenyl-3-hydroxydecane-6-sulfonic, 8-isopropyl-4-hydroxyhexadecane-1-sulfonic, 4-hydroxycyclohexane-1-sulfonic, and the like acids.

EXAMPLES

The following examples further illustrate the invention.

Example 1: Sulfonation of 1-Hexadecene

The sulfonation unit consisted of a 5 mm. I.D. 3-foot, jacketed falling film reactor equipped with an inlet weir for the olefin feed, a central 3 mm. O.D. sulfur trioxide-air inlet tube, followed by a 1⅜ inch by 4 inch post reactor tube. This reactor was continuously charged with 1-hexadecene at a rate of 4.36 grams/min. Simultaneously there was added 1.87 grams/min. of $SO_3$ diluted to 5% by weight in air (an olefin/$SO_3$ mol ratio of 1.2/1). The temperature of the outer surface of the reactor wall was maintained in the range of 45° to 65°C. by circulating cooling water in the jacket. The sulfonation product was collected and chilled to 0°C. over a period of 2 hours. The product weighed 739 grams.

The infra-red (IR) spectrum of this reaction product showed the presence of both sultone and sulfonic acid. The 1,3-sultone absorbs at 1330–1350, 1190, 1155, 1000, 940, 815–880, and 620 $cm^{-1}$. The 1,4-sultone absorbs at 1330 1360, 1160, 895, 810–825, and 530 $cm^{-1}$. Unsaturated sulfonic acid absorbs at 1700, 1165, 1040, 965 and 910 $cm^{-1}$. The above peaks were present.

The NMR spectrum also showed that the product was a mixture of sultones and unsaturated sulfonic acids. Protons beta to sulfonate in the sultones absorb at 2.1–2.6 ppm.; those alpha to sulfonate in the sultones absorb at 2.8–3.2 pp.; the proton alpha to the sultone C—O bond absorbs at 4.4–4.6 ppm.; vinyl protons absorb at 5.0–5.9 ppm. All these peaks were present.

A 10 g. portion of the crude acid/sultone product was analyzed by cold neutralization (room temperature) with 13 millimoles of NaOH in aqueous alcohl followed by complete hydrolysis and neutralization at 95°C. This analysis showed the initial presence of 34% sulfonic acid and 66% sultones. The sodium salt solution obtained was deoiled by 3 extractions with petroleum ether from a 75% alcohol solution and found to contain about 0.5 weight per cent of oil. Thus, both the original sulfonation step nd the hydrolysis step were substantially complete. Foam fractionation indicated the presence of about 16% di- or polysulfonates. The IR spectrum of this salt showed the typical bands at 1180–1200, 1065, 795, 620, and 530 $cm^{-1}$ for a sulfonate salt plus a band at 965 $cm^{-1}$ from trans double-bonds.

Example 2: Oligomerization of the Hexadecene-$SO_3$ Reaction Product

The acid reaction product from Example 1, 50 grams, was heated in a round bottomed flask at 150°–153°C. for 2¼ hours. At the end of this time, the viscosity of the heated material was considerably greater than that of the starting material.

An infra-red spectrum showed strong adsorptions at 1700, 1165, 1040, 910 $cm^{-1}$, all of which are typical of aliphatic sulfonic acids. The absence of adsorption bands at 1330–1360, 895 and 810–880 $cm^{-1}$ showed that the sultone originally present in the feed stock had all been converted. The absence of a 965 $cm^{-1}$ adsorption band showed that there were no 1,2-disubstituted double bonds, i.e., all alkene-sulfonic acid was converted.

A nuclear magnetic resonance (NMR) spectrum had adsorption at 2.9–3.2 ppm, typical of aliphatic sulfonic acids. The absence of any bonds at 4.4–4.6 ppm and at 5.0–5.9 ppm also indicate complete conversion of the sultone and the absence of any 1,2-disubstituted double bonds, respectively.

A neutralization equivalent analysis required 0.0032 mols of base per gram of product.

The product was shown to have 2.3% water by a Karl Fisher titration.

The remainder of the product was converted to the sodium salt and was then desalted by precipitation from 70% aqueous ethanol and deoiled by 5 extractions of this solution with petroleum ether. The precipitae was analyzed for $Na_2SO_4$ and the extract was concentrated. This procedure showed the presence of 1.5% (wt.) oil and 0.4% sodium sulfate in the reaction mixture. The I.R. spectrum of the sulfonate salt was typical of the IR spectrum of olefin sulfonate salts, except there was not adsorption at 965 $cm^{-1}$, i.e., there were no double bonds of the trans configuration.

Example 3: Esterification of the Oligomerization Product of Example 2

A portion of the product of Example 2, 5.00 grams, was dissolved in about 250 ml. of diethyl ether. Then diazomethane formed by the decomposition of N-methyl-N-nitroso-p-toluenesulfonamide [Reference: Rec. Trav. Chem. 73, 229 (1954)] was bubbled into the ether solution until the solution had a persistent yellow color. This solution was filtered to give 0.08 grams of an insoluble residue. Then the ether was removed from the filtrate by evaporation to give 5.26 grams of viscous brown liquid. Infra-red and NMR analyses were run on this ester. The infra-red spectrum showed adsorption bands at 1360, 1170, and 995 cm$^{-1}$, all of which are characteristic of methyl aliphatic sulfonate esters. There were no noticeable adsorptions characteristic of sultone or of trans olefinc double bonds in the ester. There were no hydroxyl adsorption bands at 3200–3700 cm$^{-1}$. There were no ether adsorption bands at 1060–1150 cm$^{-1}$.

The molecular weight of the oligomer ester was found to be 627 by the thermoelectric measurement of vapor pressure (Reference: ASTM D 2503-67), and the highest mass peak obtained from a mass spectral analysis was 638 mass units.

Example 4: Preparation and Separation of SO$_3$-Hexadecene Sulfonation Product A 1-hexadecene-SO$_3$ reaction product was prepared as in Example 1 except that less SO$_3$ (1.20 g/min.) was used, resulting in an SO$_3$/olefin mole ratio of 0.77/1. The product was collected in about 4 volumes of n-pentane. As in Example 1, a portion of this product was analyzed by neutralization, hydrolysis, desalting, deoiling and foam fractionation to show that the original sulfonation product contained about 50% sultone, 24% sulfonic acid, 1% disulfonate, and 25 mole % unreacted olefin.

Another portion (50 ml.) of the above pentane solution was filtered at room temperature to recoever 0.66 g of crystalline hexadecane-1,3-sultone, and then cooled in an ice bath and refiltered to recover another 1.00 g. of hexadecane-1,3-sultone. The remaining pentane filtrate was mixed with 21 ml. H$_2$O and 75 ml. acetone and extracted five times with n-pentane to give another 4.0 g of sultone (mixed with 2.4 g. unreacted olefin). The sultone fractions were combined.

The aqueous-acetone layer which contained the sulfonic acid fraction of the product was stripped of solvents at 40°–45°C. under a vacuum to give 2.85 g. of viscous acid identified as hexadecene sulfonic acid on the basis of an IR spectrum which showed the presence of trans olefinic double bond (965 cm$^{-1}$) and the absence of sultones (no 830 and 530 cm$^{-1}$ bands).

Example 5: Dimerization of Hexadecene Sulfonic Acid

The sulfonic acid prepareed in Example 4 (1.42 g) was heated at 160°C. for 2 hours. The reaction product had IR and NMR spectra, which for all practical purposes was identical to that of the acid product of Example 2.

Example 6: Dimerization of Hexadecane-1,3-Sultone

Hexadecane-1,3-sultone (10 g, twice recrystallized from petroleum ether) was heated for 2 hours at 157°–187°C. The IR and NMR spectra was essentially identical to that of the acid product of Example 2. The oligomeric acid was methylated as in Example 3. Carbon-hydrogen analyses on the methyl ester were 63.58% C, 10.52% H. Theoretical for C$_{34}$H$_{68}$S$_2$O$_6$ is 64.10% C, 10.76%.

The NMR spectrum of the methyl ester showed adsorption at 6.6–7.0 ppm corresponding to the presence of substantial amounts of hydrogen atoms bonded to aromatic ring carbon atoms. Assuming a tetrasubstitute aromatic ring, this corresponds to about 15 mol per cent of the product; similar adsorptions were observed in the NMR spectra of the products of Example 2, 3 and 5.

Example 7: Oligomerization of SO$_3$-Octene-1 Sulfonate

Example 1, 2 and 3 were repeated except that the 1-olefin used was 1-octane and the sulfonation mole ratio was 0.25 moles S,O$_3$ per mole of olefin. The excess octene was removed from the sulfonation product under vacuum at 40–45°C. The oligomerization was conducted for 2 hours at 160°–164°C. IR and NMR spectra of the acid and methyl ester were the same as obtained for the 1-hexadecene product except for the effect of the shorter alkyl chain. The vapor pressure molecular weight value of the methyl ester was 471; the major mass spectral peaks ran up to 414.

Example 8: Effect of Excess Water on the Oligomerization

Fifty grams of the unneutralized acid product of Example 1 was placed in a Fischer-Porter bottle equipped with a magnetic stirrer along with 10 grams of water. The mixture was heated to 150°C. and stirred at this temperature for 6 hours. At the end of this time cold neutralization with NaOH required 3.08 millimols/g. Deoiling as before showed that sulfonic acid had been formed and that only 10% of the original sultone remained. In this case, in contrast to Example 2, the material had not been oligomerized, but had been simply hydrolyzed to alkene- and hydroxyalkane-sulfonic acid. Both the acid and the sodium salt showed substantial 965 cm$^{-1}$ peaks in the IR spectrum. Analytical hydrogenation of the salt showed the presence of about 67% alkene-sulfonate. The presence of hydroxyl groups was demonstrated by converting the hydroxyalkane acid component back to sultone as follows. The water was removed by vacuum from a 2.01 g. sample of the above hydrolyzed acidic product, followed by heating at 100°C. for 1 hour. Cold neutralization of this product gave a neutralization equivalent of 2.47 millimoles/gram or a decrease of 31% compared with the hydrolyzed acid on a dry basis.

Example 9: Conversion of Normal Olefin Sulfonate to Methyl Ester

A 19 g. sample of normal neutralized and hydrolyzed 1-hexadecene sulfonate, as described in Example 1, in aqueous solution (25%) was subjected to the ether-HCl extraction procedure [Reference: R. House and J. L. Darragh, Anal. Chem. 26, 1492 (1954)] to convert it to the corresponding sulfonic acid dissolved in ether. The ether solution was methylated as in Example 3 to from 17.25 g. of clear, yellow oil whose IR spectrum showed substantial hydroxyl adsorption at 3200–3600 cm$^{-1}$, and large bands at 1350, 1170 and 995 cm$^{-1}$.

Example 10: Plasticization of Polyvinyl Chloride

The methyl esters of Examples 3 and 9 were mixed in a 60/40/1 ratio with a commercial polyvinyl chloride resin/ester/commercial stabilizer and pressed into sheets at 182°C. Both materials plasticized the resin. Physical properties of the plastic sheets were as follows:

|  | COMPATIBILITY | VOLATILITY, % at 200°F. - 66 HRS. |
|---|---|---|
| Example 3, Oligomer Ester | Fair | 6.3 |

| | COMPATIBILITY | -continued<br>VOLATILITY, % at<br>200°F. - 66 HRS. |
|---|---|---|
| Commercial Dioctyl Phthalate | Standard | 10.5 |
| Example 9, Olefin Sulfonate Ester | Poor | 16.3 |

These data indicate that the SO$_3$-olefin sulfonate oligomer products are useful plasticizers for polyvinyl chloride resins.

Example 11: Preparation of Mixed Olefin-SO$_3$ Reaction Mixture

The reactor used for this sulfonation consisted of a continuous falling film-type unit in the form of a vertical water-jacketed tube. Both the olefin and the SO$_3$-air mixture were introduced at the top of the reactor and flowed concurrently down the reactor. At the bottom the sulfonated product was separated from the air stream.

The olefin feed was a straight-chain 1-olefin blend produced by cracking highly paraffinic wax and having the following composition by weight: 1% tetradecene, 27% pentadecene, 29% hexadecene, 28% heptadecene, 14% octadecene and 1% nonadecene. This mixture was charged to the top of the above described reactor at a rate of 306 pounds/hour. At the same time 124.2 pounds/hour of SO$_3$ diluted with air to 3% by volume concentration of SO$_3$ was introduced into the top of the reactor. The reactor was cooled with water to maintain the temperature of the effluent product within the range of 43°–46°C. The average residence time of the reactants in the reactor was less than 2 minutes.

After passing out of the sulfonation reactor the sulfonated product was mixed with 612 pounds/hour or 11.2% aqueous caustic and heated to 145°–150°C. in a tubular reactor at an average residence time of 30 minutes in order to hydrolyze and neutralize the sulfonated product. Olefin sulfonates were produced at the rate of 463 pounds per hour as an aqueous solution having a 45% by weight solids content and a pH of 10.8.

A portion of this product was analyzed and shown to be made up of the sodium salts of alkene sulfonic acids, hydroxyalkane sulfonic acids, and disulfonic acids. These three major components were present in a weight ratio of about 50/35/15, respectively.

After operating in the above-described manner for several hours, the neutralization and hydrolysis vessels were replaced by a collecting tank, and the acid reaction product was collected for use as a feed for the oligomerization reaction.

Example 12: Oligomerization of n-C$_{14}$-C$_{19}$ Mixed Olefin-SO$_3$ Sulfonate The acid product from Example 11 was heated at 150 to 155°C. for 3 hours. At the end of this time an infrared analysis indicated that essentially all sultone and alkene sulfonic acid had been converted to oligomeric acids. This reaction mixture was neutralized to a pH of 7 to 8 using 8% aqueous caustic. The resulting solution was dried to give the sodium salt which contained only about 7% non-surface active material as measured by a cationic titration.

Example 13: Foam Stability of the Oligomeric Sulfonic Acid Salts and Mixtures Thereof The neutralized reaction product from Example 12, 43 parts, was dissolved in 57 parts of a 2/1 mixture of water and isopropyl alcohol. One-half gram of the resulting test solution was dissolved in 100 ml of water in a 600 ml graduated beaker. The solution was stirred rapidly for 1 minute with an efficient stirrer. This procedure converted essentially all of the liquid into foam. The maximum volume of foam and the time required for 50 ml of liquid to drain from the foam were measured (Run No. 1). The same experiment was also carried out on a mixture consisting of 24 parts of the neutralized product of Example 12 and 16 parts of the neutralized monosulfonate prepared in Example 11 (Run No. 2) dissolved in 60 parts of the water isopropanol solvent. Two other experiments (Runs 3 and 4) were carried out using 1 gram portions of the two test solutions dissolved in 100 ml of water. The same four experiments were then carried out with 10 ml of added kerosene. The results are given in the following table:

| | TEST SOLUTION | | WITHOUT KEROSENE | | WITH KEROSENE | |
|---|---|---|---|---|---|---|
| Run No. | Gms/100 Ml Water | Composition | Initial Initial Foam (Ml) | Time for 50% Drain (Min.) | Initial Foam (Ml) | Time for 50% Drain (Min.) |
| 1 | 0.5 | Oligomer Sulfonate | 400 | 3-1/6 | 375 | 3-1/3 |
| 2 | 0.5 | Oligomer Sulfonate/ Monosulfonate | 400 | 3-5/6 | 400 | 4-5/6 |
| 3 | 1.0 | Oligomer Sulfonate | 450 | 3-1/3 | 450 | 4-1/3 |
| 4 | 1.0 | Oligomer Sulfonate/ Monosulfonate | 475 | 4-1/6 | 500 | 5-1/3 |

These data demonstrate that olefin sulfonate oligomers are excellent foaming agents, being particularly suitable for use in the preparation of foamed oil well circulation fluids. The oligomer-monomer sulfonate mixtures moreover, yield even better foamed well circulation fluids.

Example 14: Effect of Water on Oligomerization Reaction

Stainless steel tubes having a capacity of 15 ml were charged with 10 grams of a test solution made up of the olefin/SO$_3$ reaction mixture from Example 11 and water. The tubes were sealed and inserted horizontally into a large metal block maintained at a temperature of 150°C. The entire block with the enclosed tubes was shaken at a rate of 150 cycles per minute, for 2 hours. Then the tubes were quenched by immersion into cold water.

The contents of each tube were removed and checked for appearance and viscosity. A weighed portion of each test mixture, about 0.4–0.45 grams, was dissolved in 50 ml of ethanol and neutralized with 0.1 $n$ NaOH. The resulting solution was then diluted to 100 ml with water and examined for solubility. The increasing presence of unconverted, neutral, water insoluble alkane sultone was observed as the water content present during oligomerization increased:

| TEST SOLUTION | | REACTION PRODUCT | |
| --- | --- | --- | --- |
| Reaction Mix. (Grams) | H$_2$O (Grams) | Viscosity | Appearance of Sodium Salt in 50% Aq. Ethanol |
| 10 | 0 | Most Viscous | Clear |
| 9.9 | 0.1 | Less Viscous | Slight Haze |
| 9.7 | 0.3 | Least Viscous | Cloudy |
| 9.5 | 0.5 | Semi-Solid | Separate Insol. Layer |
| 9.3 | 0.7 | Semi-Solid | Separate Insol. Layer |
| 9.0 | 1.0 | Semi-Solid | Separate Insol. Layer |

Example 15: Effect of Temperature on Oligomerization Reaction

A 500 ml 3-inch round bottom flask, equipped with a paddle stirrer, a nitrogen inlet, thermometer and gas outlet tube was heated to about 5°–10°C. above the desired temperature. Nitrogen gas was passed slowly through the flask. Then an olefin/SO$_3$ reaction mixture made as in Example 11 and weighing about 200 grams, was charged to the flask. The reaction mixture was stirred with nitrogen flowing over the surface. Samples were removed periodically and cooled to room temperature.

Each sample was checked for color and viscosity, and an 0.4 to 0.5 gram sample was titrated with 0.1 NaOH to determine the acid content. Another small portion was titrated for anionic surface active components with a standard cationic surfactant.

The extent of reaction at various times was determined for runs at four temperatures:

| Temp. °C. | Time to 25% Conversion (Hrs.) | Time to 75% Conversion (Hrs.) |
| --- | --- | --- |
| 20 | 5.5 | 10.0 |
| 140 | 0.8 | 1.4 |
| 160 | — | 0.4 |

These data demonstrate that temperature effects in the oligomerization herein are the usual time-temperature relationship, i.e., roughly a doubling of reaction rate occurs for each 10°C. increase in reaction temperature.

Examples 16–22

A series of sultones were prepared and oligomerized by heating at 170°C. for 4 hours in the apparatus of Example 14. The neutral and free sultones were recovered from the crude reaction product of the air-diluted sulfur trioxide sulfonation of the olefins, decene-1, dodecene-1, tetradecene-1, hexadecene-1, octadecene-1, eicosene-1 and docosene-1. The extraction technique employed for the separation of the sultones was as described in Example 4. In each case the oligomerizations were substantially completed in the 4 hour reaction period.

Examples 23–27: Oligomers as Built Detergents

The surface active nature of the present oligomers, particularly the $C_{28}$-$C_{40}$-disulfonates, i.e., oligomers of the $C_{14}$-$C_{20}$ sultones, in built detergent formulations was demonstrated as follows. Representative oligomers obtained in Examples 6 and 16–22 were each neutralized with aqueous caustic and then evaporated to dryness to give the corresponding solid sodium salts. These salts were each compounded into a detergent formulation having the following composition in parts by weight: 25 parts of the sodium salt of the polysulfonic acid, 7 parts sodium silicate, 1 part carboxy methyl cellulose, 8 parts water, and 59 parts sodium sulfate. The resulting compositions were each dissolved in 50 ppm hard water to give an 0.1% concentration which was then tested for detergency. In this detergency test, the soil removal efficiency of a test material is related to that of a good and a bad standard. The good standard is arbitrarily assigned a detergency rating of 6 and the poor standard a rating of 2. Then the test materials are given values on the same sclae according to their relative detergencies compared to the standards. The results of this detergency test are given in the following table:

| Example No. | Active Component | Relative Detergency |
| --- | --- | --- |
| 23 | $C_{10}$-Sultone Oligomer | 2.2 |
| 24 | $C_{12}$-Sultone Oligomer | 2.3 |
| 25 | $C_{14}$-Sultone Oligomer | 4.3 |
| 26 | $C_{16}$-Sultone Oligomer | 4.0 |
| 27 | $C_{18}$-Sultone Oligomer | 4.6 |

These data demonstrate that the subject sulfonate oligomers and particularly those of the $C_{14}$ to about the $C_{30}$ sultones, hydroxyalkane sulfonic acids and the alkene sulfonic acids or mixtures thereof are useful built detergents. Individual molecular weight, i.e., C-number species and mixtures or fractions of the $C_{10}$-$C_{30}$-oligomers are also useful. Other builders such as sulfate salts, phosphate builders and phosphate-free builders, as known in the art, are also suitable for the compounding of built detergents with the present novel oligomeric sulfonic acid salts (i.e., the usual water soluble alkaline salts such as the alkali metal salts, e.g., sodium and potassium; the ammonium salts the calcium and magnesium salts and the like, as known in the detergent art). The unneutralized oligomers herein, i.e., the disulfonic acids per se are useful as the foaming agent for the production of preformed acidic well circulation fluids, particularly in the oil well servicing art.

Examples 28–34

In the use of foaming agents for the preparation of foamed well circulation fluids liquid concentrates of the surface active agent are ordinarily employed provided that phase separations, particularly solid formations, do not occur upon standing or at the low temperatures often encountered at the wellhead in the field. These examples demonstrate that liquid concentrates of mixtures of the subject oligomers with the precursor monomer or of the oligomers per se are useful foaming agents having excellent low temperature characteristics. The olefin sulfonate monomer used in these examples was the $C_{14}$-$C_{19}$-product obtained by base hydrolysis of the product described in Example 11. The oligomer used was the product obtained as described in Example 12. The liquid concentrates tested contained 40 parts (weight) water, 20 parts isopropanol and 40 parts of the active, as noted in the table below. These concentrates were cooled to 0°C. with the results as also noted in the table below.

| Example No. | Oligomer-Monomer Weight Ratio | Observation |
|---|---|---|
| 28 | 0/100 | Rapid Solidification |
| 29 | 20/80 | Rapid Solidification |
| 30 | 30/70 | Slow Solidification |
| 31 | 40/60 | Slow Solidification |
| 32 | 50/50 | Mostly Liquid. Some Suspended Solids |
| 33 | 60/40 | Clear Solution |
| 34 | 100/0 | Clear Solution |

When other lower alcohols (i.e., alcohols having less than 4 carbon atoms) such as methanol, ethanol, n-propanol and mixtures thereof are used as the cosolvent, similar results are obtainable.

The foregoing examples demonstrate that the subject disulfonate oligomers per se yield liquid detergent concentrates having excellent low temperature characteristics, e.g., solubility etc. Similarly, these data demonstrate that the subject oligomeric disulfonates are useful as additives for the improvement of the low temperature characteristics of sulfonate detergent actives whose liquid concentrates have poor low temperature solubilities.

We claim:
1. In a method of circulating a gas-in-liquid foam in a well the improvement which comprises generating said foam from a gas and a foamable aqueous solution containing as foaming agent the oligomer obtained by the process which comprises heating in the liquid phase a feed comprising at least one compound having a carbon atom content of at least 5 but less than 50 selected from the group of the formula a) 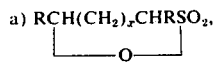

b. $RCH(OH)(CH_2)_xCHRSO_3H$, and c. $RCH{=}CH(CH_2)_yCHRSO_3H$ wherein $x$ is the number 0 and integers 1–3 and $y$ is a whole number in the range 0–$n$ wherein $n$ is a number which is 4 less than the number of carbon atoms in the longest straight chain of the compound containing the —$SO_3H$ group as a substituent, and wherein the several R groups are the same or different and are hydrogen or alkyl hydrocarbon radicals; said heating being at a temperature above about 110°C and below the carbonization temperature of the feed, in the substantial absence of water, and for a period at least sufficient for a significant conversion of the feed to the corresponding oligomeric disulfonic acids, said oligomer being neutralized with ammonia, an alkali metal base, a calcium base, a magnesium base, or a mixture thereof and circulating said foam in said well.

2. The method as in claim 1 wherein said temperature is in the range from about 120°C to 200°C and said feed compounds contain from about 5 to 30 carbon atoms.

3. The method as in claim 2 wherein said feed is of the sultone group.

4. The method as in claim 2 wherein said feed is of the hydroxy sulfonic acid group.

5. The method as in claim 2 wherein said feed is of the alkene sulfonic acid group.

6. The method as in claim 1 wherein said heating is continued until the ratio of the nuclear magnetic resonance absorbance of

[2(3.4 to 3.7 ppm + 4.4 to 4.6 ppm) ÷ 5.0 to 5.9 ppm]

for the feed and resulting product mixture has decreased to less than about 0.90 to 1, respectively.

* * * * *